(12) United States Patent
Kajita et al.

(10) Patent No.: US 8,465,919 B2
(45) Date of Patent: Jun. 18, 2013

(54) METHOD OF DETECTING METHYLATED CYTOSINE

(75) Inventors: Masahiro Kajita, Kobe (JP); Noriko Oka, Kobe (JP); Noriaki Yamamoto, Kobe (JP); Ayako Sakai, Kobe (JP); Hideki Ishihara, Miki (JP)

(73) Assignee: Sysmex Corporation, Kobe (JP)

( * ) Notice: Subject to any disclaimer, the term of this patent is extended or adjusted under 35 U.S.C. 154(b) by 304 days.

(21) Appl. No.: 12/674,648

(22) PCT Filed: Aug. 20, 2008

(86) PCT No.: PCT/JP2008/064826
§ 371 (c)(1),
(2), (4) Date: Feb. 22, 2010

(87) PCT Pub. No.: WO2009/025296
PCT Pub. Date: Feb. 26, 2009

(65) Prior Publication Data
US 2010/0240042 A1  Sep. 23, 2010

(30) Foreign Application Priority Data

Aug. 23, 2007 (JP) .................. 2007-217263

(51) Int. Cl.
*C12Q 1/68* (2006.01)
*C07H 21/00* (2006.01)
*C07H 21/02* (2006.01)
*C07H 21/04* (2006.01)

(52) U.S. Cl.
USPC .......... 435/6.1; 536/22.1; 536/23.1; 536/24.3

(58) Field of Classification Search
USPC .......................................... 435/6.1; 536/22.1
See application file for complete search history.

(56) References Cited

U.S. PATENT DOCUMENTS 5,681,941 A * 10/1997 Cook et al. .................. 536/23.1
2002/0042077 A1  4/2002 Ellson
2003/0153737 A1  8/2003 Manoharan et al.

FOREIGN PATENT DOCUMENTS

JP  2004-337042 A   12/2004
WO  2004/101823 A1  11/2004
WO  2006/132022 A1  12/2006

OTHER PUBLICATIONS

Matthews et al. Review : Analytical Strategies for the use of DNA probes. Analytical Biochemistry 169 : 1-25 (1988).*
Okamoto, A. 5-Methylcytosine—selective osmium oxidation Nucleosides, Nucleotides and Nucleic Acids 26 : 1601 (2007).*
Tanaka et al. Direct labeling of 5-Methylcytosine and its applications. JACS 129 :5612 (Apr. 2007).*
Tainaka et al. Develpoment of bipyridine modified nucleobase for methylcytosine-sensirtive crosslink reaction. Nucleic Acids Symposium Series No. 50 : 129 (2006).*
Extended European Search Report issued Dec. 29, 2010, in EP 08827745.4.
Akimitsu Okamoto, et al., "Sequence-selective osmium oxidation of DNA: efficient distinction between 5-methylcytosine and cytosine", Org. Biomol. Chem., 2006, pp. 1638-1640, vol. 4.
Chinh T. Bui, et al., "Chemical cleavage reactions of DNA on solid support: application in mutation detection" BMC Chemical Biology, 2003, pp. 1-6, vol. 3.
James G. Herman, et al., "Methylation-specific PCR: A novel PCR assay for methylation status of CpG islands", Proc. Natl. Acad. Sci., Medical Sciences, Sep. 1996, pp. 9821-9826, vol. 93.

* cited by examiner

*Primary Examiner* — Ethan C Whisenant
(74) *Attorney, Agent, or Firm* — Sughrue Mion, PLLC

(57) ABSTRACT

The method for detecting a methylated cytosine of the present invention comprises the steps of:

hybridizing a sample DNA with an oligonucleotide which can hybridize with a region of the sample DNA containing a cytosine suspected of being methylated and has an a basic site at the position complementary to the cytosine;

reacting the hybridized sample DNA obtained in the previous step with an oxidizing agent to oxidize the cytosine when it is methylated; and detecting the oxidized methylated cytosine.

12 Claims, 1 Drawing Sheet

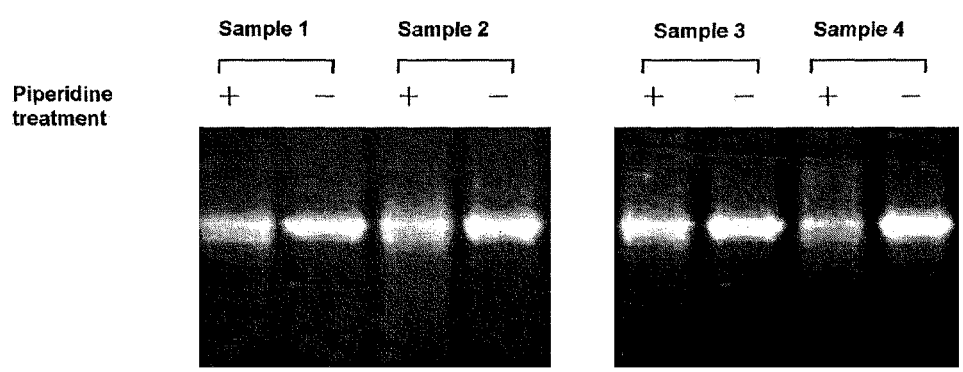

SEQUENCE LISTING

```
<160> NUMBER OF SEQ ID NOS: 4

<210> SEQ ID NO 1
<211> LENGTH: 50
<212> TYPE: DNA
<213> ORGANISM: Artificial Sequence
<220> FEATURE:
<223> OTHER INFORMATION: chemical synthesis nucleotide

<400> SEQUENCE: 1
gaggccttcg ctggagtttc gccgccgcag tcttcgccac cagtgagtac            50

<210> SEQ ID NO 2
<211> LENGTH: 50
<212> TYPE: DNA
<213> ORGANISM: Artificial Sequence
<220> FEATURE:
<223> OTHER INFORMATION: chemical synthesis nucleotide
<220> FEATURE:
<221> NAME/KEY: misc_feature
<222> LOCATION: (20)..(20)
<223> OTHER INFORMATION: "n" represents m5c
<220> FEATURE:
<221> NAME/KEY: misc_feature
<222> LOCATION: (23)..(23)
<223> OTHER INFORMATION: "n" represents m5c
<220> FEATURE:
<221> NAME/KEY: misc_feature
<222> LOCATION: (26)..(26)
<223> OTHER INFORMATION: "n" represents m5c
```

-continued

```
<400> SEQUENCE: 2
gaggccttcg ctggagttn gcngcngcag tcttcgccac cagtgagtac            50

<210> SEQ ID NO 3
<211> LENGTH: 50
<212> TYPE: DNA
<213> ORGANISM: Artificial Sequence
<220> FEATURE:
<223> OTHER INFORMATION: chemical synthesis nucleotide

<400> SEQUENCE: 3
gtactcactg gtggcgaaga ctgcggcggc gaaactccag cgaaggcctc            50

<210> SEQ ID NO 4
<211> LENGTH: 50
<212> TYPE: DNA
<213> ORGANISM: Artificial Sequence
<220> FEATURE:
<223> OTHER INFORMATION: chemical synthesis nucleotide
<220> FEATURE:
<221> NAME/KEY: misc_feature
<222> LOCATION: (23)..(23)
<223> OTHER INFORMATION: "n" represents dSpacer

<400> SEQUENCE: 4
gtactcactg gtggcgaaga ctngcgcggc gaaactccag cgaaggcctc            50
```

METHOD OF DETECTING METHYLATED CYTOSINE

CROSS REFERENCE TO RELATED APPLICATIONS

This application is a National Stage of International Application No. PCT/JP2008/064826 filed Aug. 20, 2008, claiming priority based on Japanese Patent Application No. 2007-217263, Aug. 23, 2007, the contents of all of which are incorporated herein by reference in their entirety.

TECHNICAL FIELD

The present invention relates to a method for detecting a methylated cytosine in a sample DNA, and an oligonucleotide used for the method.

BACKGROUND ART

In chromosomal DNA of higher eukaryotic organisms, the 5-position of cytosine (C) among the bases constituting DNA may be methylated in some cases. Methylation of DNA in the higher eukaryotic organisms functions as a mechanism for controlling the expression of genetic information. For example, when a region with many CpG sequences which is generally found in promoter regions of genes (CpG island) is methylated, transcription of these genes is suppressed. On the other hand, when the CpG island is not methylated, transcription factors can bind to the promoter region and then the genes can be transcribed.

Thus, methylation of DNA is one of the regulating mechanisms of the gene expression. Due to this, methylation of DNA plays important rolls in various physiological and pathological phenomena such as early embryogenesis, tissue specific gene expression, genomic imprinting and inactivation of X chromosomes which are characteristic phenomena of mammals, stabilization of chromosomes, the timing of DNA replication and the like. Recently, it has been found that methylation of DNA is strongly relevant to cancers and other diseases.

A methylation specific polymerase chain reaction method is known as the method for analyzing methylation of DNA (see James G. HERMAN et al., Methylation-specific PCR: A novel PCR assay for methylation status of CpG islands, Proc. Natl. Acad. Sci. USA, Vol.93, pp. 9821-9826, September 1996). In this method, a methylated cytosine and non-methylated cytosine are differentiated by converting the non-methylated cytosine to another base with a reagent that can convert bases such as bisulfites. However, it is known that such conversion treatment of DNA with the base-converting reagent degrades most of DNAs in biological samples due to the chemical reaction.

Recently, a method for detecting methylation of cytosine in a DNA sample is disclosed in which the DNA sample is hybridized with a guide probe such that the cytosine suspected of being methylated in the DNA sample forms a bulge structure or a mismatch, the methylated cytosine in the bulge structure or the mismatch is then specifically oxidized with an oxidizing agent such as osmates, and the oxidized product is detected (see WO 2006/132022). This method allows the detection of a methylated cytosine by utilizing the fact that the methylated carbon atom in pyrimidine ring on the methylated cytosine is liable to be oxidized, thereby detecting the oxidized product.

When a DNA sample is treated with an oxidizing agent, methylated cytosines other than the target methylated cytosine and thymines that have a methyl group similar to methylated cytosines are also oxidized. In order to avoid the oxidization of bases other than target bases, base pairs are formed between the guide probe and the bases in the DNA sample other than the target bases by hybridization of the guide probe and the DNA sample.

However, when the bulge structure or the mismatch is formed between the DNA sample and the guide probe, a steric distortion may be generated in the double helix structure after hybridization. More specifically, in the bulge structure, the cytosine which is targeted for the detection of methylation projects from a double-stranded DNA formed by hybridization of the DNA sample and the guide probe. Due to this steric reason, the base adjacent to the bulge structure in the DNA sample is difficult to form a base pair with the corresponding base in the guide probe. In case of the guide probe which forms the mismatch, the base adjacent to the mismatch is also difficult to form a base pair with the corresponding base in the guide probe because of the steric hindrance of the base which does not form a base pair with the target cytosine for detection. When thymine is present in a region adjacent to the cytosine suspected of being methylated and when the DNA sample contains CpG island, in particular, it is highly probable that the steric distortion is generated. Accordingly, the bases other than the target base in the DNA sample and the guide probe may not sufficiently form base pairs, and thymines which are not targeted may possibly be oxidized.

When the detection of methylated cytosine is used as a diagnosis of cancers or other diseases, highly precise detection is required in view of the reliability of the diagnosis results. Therefore, there has been a need to make an improvement in accuracy of the detection of methylated cytosines.

DISCLOSURE OF THE INVENTION

Problems that the Invention is to Solve

In view of the above situation, an object of the present invention is to provide a precise method for detection of a methylated cytosine using an oligonucleotide which has little tendency to produce a steric distortion and allows an easy base-pair formation for the bases other than the cytosine suspected being methylated when it is hybridized with a sample DNA.

Another object of the present invention is to provide an oligonucleotide used for the methylated cytosine detection which is used in the above method for detection of a methylated cytosine.

Further object of the present invention is to provide a nucleotide chip for detection of a methylated cytosine comprising a solid support on which the above oligonucleotide is fixed.

Means for Solving the Problems

As a result of the diligent study in view of the above situation, the present inventors have found that an oligonucleotide which has an abasic site at the position complementary to a cytosine suspected of being methylated in a sample DNA can hybridize with the sample DNA without steric distortion. The present inventors have also found that the methylated cytosine in the sample DNA can be further specifically oxidized with an oxidizing agent when the sample DNA is hybridized with the above oligonucleotide and achieved the present invention.

Thus, the present invention is to provide:
(1) a method for detecting a methylated cytosine comprising the following steps of:
hybridizing a sample DNA with an oligonucleotide which can hybridize with a region of the sample DNA containing a cytosine suspected of being methylated and has an abasic site at the position complementary to the cytosine;

reacting the hybridized sample DNA obtained in the previous step with an oxidizing agent to oxidize the cytosine when it is methylated; and detecting the oxidized methylated cytosine;

(2) the method according to (1), wherein the step of detecting comprises the steps of treating the sample DNA having been reacted with the oxidizing agent with a basic compound, and determining the occurrence of a cleavage in the sample DNA which has been treated with the basic compound;

(3) the method according to (2), wherein the basic compound is piperidine or aniline;

(4) the method according to (2) or (3), wherein the step of determining comprises the steps of amplifying the region of the sample DNA containing the cytosine suspected of being methylated, and detecting the amplified product obtained from the step of amplifying;

(5) the method according to any one of (1) to (4), wherein the oxidizing agent is at least one selected from a permanganate, an osmate, a tungstate, a periodate, hydrogen peroxide solution, t-butyl hydroperoxide, perbenzoic acid, a perbenzoic acid derivative, iodine, a rhenium oxide, peracetic acid, a peracetic acid derivative and a manganese-salen complex;

(6) the method according to (5), wherein the oxidizing agent is the osmate;

(7) the method according to (6), wherein the oxidized methylated cytosine forms an osmium complex with the osmate;

(8) the method according to (1), wherein the oxidizing agent is an osmate; the step of reacting with the oxidizing agent further comprises reacting the sample DNA that has been reacted with the oxidizing agent further with a compound which can, be a ligand of an osmium ion; and the step of detecting detects the methylated cytosine which forms an osmium complex to which the ligand is bound via a coordinate bond;

(9) the method according to (8), wherein the ligand is labeled with a labeling substance;

(10) the method according to (8) or (9), wherein the ligand is pyridine, bipyridine or phenanthroline;

(11) an oligonucleotide usable in a method for detecting a methylated cytosine comprising treating a sample DNA with an oxidizing agent and detecting an oxidized methylated cytosine, which can hybridize with a region of the sample DNA containing a cytosine suspected of being methylated and has an abasic site at the position complementary to the cytosine;

(12) the oligonucleotide according to (11), wherein the cytosine is in a CpG island region;

(13) the oligonucleotide according to (11) or (12), wherein the abasic site is constructed by a nucleotide without a base;

(14) the oligonucleotide according to any one of (11) to (13), which forms a base pair with all thymine(s) present in a region of the sample DNA which can hybridize with the oligonucleotide; and

(15) a nucleic acid chip for detecting a methylated cytosine using an oxidizing agent, comprising a solid support on which the oligonucleotide according to any one of (11) to (14) is fixed.

Effect of the Invention

According to the present invention, an oligonucleotide for detecting a methylated cytosine, which generates little steric distortion and is easy to form a base pair with a base other than the cytosine suspected of being methylated when it is hybridized with a sample DNA, and a nucleic acid chip using the same can be provided.

When the detection of a methylated cytosine using an oxidizing agent is carried out with the oligonucleotide or nucleic acid chip, the oxidization of a base other than the cytosine suspected of being methylated in the sample DNA such as thymine is prevented. As a result, it is possible to more specifically oxidize the methylated cytosine, improving an accuracy of the detection of a methylated cytosine.

The oligonucleotide and nucleic acid chip of the present invention are useful when the sample DNA is a DNA having thymine in a region adjacent to the target cytosine, and when the sample DNA is a DNA containing CpG island.

According to the present invention, the precise method for detecting a methylated cytosine is provided using the oligonucleotide for detecting a methylated cytosine.

By using the method for detecting a methylated cytosine according to the present invention, it is possible to precisely detect only the methylated cytosine because oxidization with an oxidizing agent of a base other than cytosine suspected of being methylated in the sample DNA such as thymine is sufficiently prevented.

BRIEF DESCRIPTION OF DRAWING

FIG. 1 represents the results of electrophoresis of Samples 1 to 4 after osmium oxidization reaction and piperidine treatment.

BEST MODE FOR CARRYING OUT THE INVENTION

<Hybridization Step>

The method for detecting a methylated cytosine of the present invention comprises the step of hybridizing a sample DNA with an oligonucleotide which can hybridize with a region of the sample DNA containing a cytosine suspected of being methylated and has an abasic site at the position complementary to the cytosine (hereinafter also referred to as the "hybridization step").

In the present embodiment, the sample DNA is not specifically limited so long as it comprises DNA, and is preferably the one comprising a biological genomic DNA, and more preferably, the one comprising a DNA which can provide a clinical evaluation such as a diagnosis of a disease and the like. The sample DNA may include a DNA obtained from a clinical specimen, and specifically, a DNA obtained from blood, serum, lymph fluid, urine, nipple discharge, bodily fluid, tissue taken from an operation or biopsy. The sample DNA is particularly preferably the one comprising a DNA obtained from a tumor cell.

More specifically, when the detection of tumor is intended in order to obtain a clinical evaluation, the sample DNA may include a genomic DNA which controls the expression of tumor suppressor genes or oncogenes. When the detection of other diseases is intended, a genomic DNA which controls the expression of a gene relevant to the diseases may be mentioned. For example, the genomic DNA relevant to the tumor detection may include 14-3-3, MGMT, CDH13, HIC1, Twist, p16, Rassf1a, ERa, RARb, CDH1, GSTP1, Cyclin D2, DAPK, HIN1, p14 and the like. Further preferably, the sample DNA contains a CpG island region of these control genomic DNAs. The sequences of these genomic DNAs are available from public databases.

The sample DNA may contain one or more cytosines suspected of being methylated.

The oligonucleotide according to the present embodiment can hybridize with a region of the sample DNA containing a cytosine suspected of being methylated and has an abasic site at the position complementary to the cytosine. The oligonucleotide may be either of DNA and RNA, and is preferably DNA.

Thus, the sequence of the oligonucleotide is complementary to a part or whole of the nucleotide sequence of the sample DNA containing the cytosine suspected of being methylated, and include an abasic site at the position complementary to the cytosine.

As used herein, "cytosine suspected of being methylated" refers to a target cytosine for which the methylation thereof is sought to be detected. The cytosine in the sample DNA may be methylated or not methylated, and when methylated, it can be 5-methylcytosine or 6-methylcytosine.

As used herein, "abasic site" has the same meaning as that is generally recognized in the art. Namely, an abasic site is a site which can not form a base pair via a hydrogen bond in a double stranded nucleic acid, due to the absence of a base in a nucleotide in one nucleic acid strand which is complementary to a certain nucleotide in another nucleic acid strand. More specifically, such abasic site can be constructed by a nucleotide structure from which a base moiety is omitted or a nucleotide having a similar structure thereto.

A compound which can form an abasic site at the position complementary to the cytosine suspected of being methylated in the sample DNA is not specifically limited so long as it is a compound which can, when double-stranded nucleic acid is formed by hybridization of the oligonucleotide and the sample DNA, form an abasic site at the position complementary to the cytosine suspected of being methylated in the sample DNA, but does not generate steric distortion in double-stranded nucleic acid. The phrase "(which) does not generate steric distortion in double-stranded nucleic acid" means a state where, upon hybridization of the sample DNA with the oligonucleotide, the base(s) in the sample DNA other than the cytosine complementary to the abasic site can form base pair(s) with the base(s) in the oligonucleotide without steric hindrance, so that the double helix structure can be formed as a whole.

The abasic site can be formed by preparing the oligonucleotide so as to a substance which can generate a space between the cytosine suspected of being methylated upon hybridization with the sample DNA is polymerized in the desired position of the oligonucleotide. Such substance includes a nucleotide without a base. By preparing the oligonucleotide with such nucleotide, abasic nucleotide structure can be formed in the oligonucleotide. Such substance is generally known as dSpacer.

The abasic site can be generated in the oligonucleotide depending on the number of cytosine suspected of being methylated in the sample DNA, and can be present at one or more positions in the oligonucleotide.

The oligonucleotide can be prepared according to a well-known nucleic acid synthesis technique. It is also known that dSpacer is inserted at the desired position in the oligonucleotide to synthesize the oligonucleotide having an abasic site. The oligonucleotides in which dSpacer is inserted are also commercially available.

The length of the oligonucleotide may be appropriately selected according to a method of detecting the oxidized methylated cytosine and to the sequence of the sample DNA, and is not specifically limited. For example, the length of 20 to 100 bases may be mentioned as the length that allows the hybridization with a region containing the cytosine suspected of being methylated in the sample DNA.

The hybridization condition can be appropriately selected according to the type of the sample DNA and the length of the oligonucleotide used. The hybridization can be carried out, for example, under the condition of pH 7 to 9, 0.001 to 0.05M of Tris-HCl, 0.05 to 0.15M of Na-ion concentration (or other salt) and at 25 to 55° C.

When the sample DNA is double-stranded DNA, it may be denatured before the hybridization step by heating the sample DNA at 90 to 100° C. for 1 to 10 minutes.

According to the method of the present invention, the methylation of the target cytosine in the sample DNA is specifically detected. Therefore, the sample DNA and the oligonucleotide are hybridized, base(s) other than the target cytosine is buried among double helix structure of double-stranded nucleic acid to create a condition where the oxidizing agent is difficult to react with the other base(s). More specifically, a thymine which is liable to react with the oxidizing agent and a methylated cytosine which is present at other position than the target cytosine in the sample DNA are allowed to form base pairs with adenine and guanine in the oligonucleotide, so that these thymine and methylated cytosine are not oxidized by the oxidizing agent. Specifically, thymine is liable to be oxidized by the oxidizing agent as similar as methylated cytosine. Thus, all thymine(s) in the sample DNA which is present in the region hybridizing with the oligonucleotide is preferably hybridized to form a base pair(s) with the oligonucleotide.

<Oxidizing Agent Reaction Step>

Due to the above hybridization step, the sample DNA hybridizes with the oligonucleotide. The method of the present invention comprises the step of reacting the hybridized sample DNA with an oxidizing agent to oxidize the cytosine when it is methylated (hereinafter also referred to as "oxidizing agent reaction step").

In the present embodiment, the oxidizing agent is not specifically limited so long as it can oxidize a double bond between carbon atoms in 5- and 6-positions of a pyrimidine ring. The oxidizing agent may include a permanganate such as potassium permanganate ($KMnO_4$), an osmate such as osmium tetraoxide ($OsO_4$) and potassium osmate (VI) ($K_2OsO_4$), a tungstate such as sodium tungstate (VI) ($Na_2WO_4$), a periodate such as sodium periodate ($NaIO_4$), hydrogen peroxide solution ($H_2O_2$), t-butyl hydroperoxide (t-BuOOH), perbenzoic acid and its derivative (m-chloroperbenzoic acid (mCPBA), 3,5-dinitroperbenzoic acid), iodine ($I_2$), rhenium oxide ($Re_2O_7$), peracetic acid (AcOOH) and its derivative and a manganese-salen complex. One or more of these may be used as the oxidizing agent.

A compound which can re-oxidize the oxidizing agent when it is reduced can be used with the oxidizing agent. The compound having such re-oxidizing property may include potassium hexacyanoferrate (III).

The condition of the treatment of the sample DNA with the oxidizing agent is not specifically limited, according to the type of the oxidizing agent, so long as a methylated cytosine can be oxidized which has not formed a base pair in the sample DNA hybridized with the oligonucleotide. For example, the oxidizing agent reaction can be carried out by adding an oxidizing agent aqueous solution having an appropriated concentration according to the type of the oxidizing agent to the hybridization product of the oligonucleotide and the sample DNA, and incubating at a temperature around 0 to 40° C. for approximately 1 minute to 1 hour.

The concentration of the oxidizing agent can be appropriately selected according to the type of the oxidizing agent and may be between 0.1 and 1000 mM, for example.

The reaction between the sample DNA hybridized with the oligonucleotide and the oxidizing agent is preferably carried out under a basic condition having pH 7 to 9. Due to this, the rate of oxidization is increased and more clear differentiation between a cytosine and methylated cytosine can be obtained. Specifically, under pH of 7 to 9, double-stranded DNA of the hybridization product between the oligonucleotide and the sample DNA is stably maintained.

<Detection Step>

The present method comprises the step of detecting the oxidized methylated cytosine obtained in the oxidizing agent reaction step (hereinafter also referred to as "detection step").

A method for detecting the oxidized methylated cytosine to be used in the present embodiment may be a known method such as described in WO 2006/132022, and is not specifically limited.

The method for detecting the oxidized methylated cytosine may include (A) a method in which the hybridization product of the oligonucleotide and the sample DNA is treated with the oxidizing agent and then with a basic compound; and (B) a method in which, when the oxidizing agent is an osmate, an osmium complex formed between the osmate and methylated cytosine is detected.

(A) Method Comprising Treatment with Basic Compound

When the method is used in which the oxidized methylated cytosine is treated with a basic compound, the detection step preferably comprises a step of treating the sample DNA with a basic compound, which has been reacted with the oxidizing agent, and a step of determining the presence of a cleavage in the sample DNA which has been treated with the basic compound.

When the sample DNA contains methylated cytosine, the oxidized methyldeoxycytidylic acid in the sample DNA produced in the oxidization reaction with the oxidizing agent is treated with the basic compound, so that a phosphodiester bond between the methylated cytosine and the adjacent nucleotide is hydrolyzed. Thus, when the cytosine is methylated in the sample DNA, the sample DNA is cleaved at the position of the methylated cytosine by the treatment with the basic compound. On the other hand, when the cytosine is not methylated, the sample DNA is not cleaved by this treatment with the basic compound. Namely, by the treatment with the basic compound, the cleavage is generated at the site of the cytosine suspected of being methylated in the sample DNA when it is methylated, so that the presence of the methylated cytosine can be detected by determining the occurrence of a cleavage in the sample DNA which has been treated with the basic compound.

The basic compound in the present embodiment is not specifically limited so long as it can hydrolyze the phosphodiester bond between the oxidized methydeoxycytidylic acid and the adjacent nucleotide in the sample DNA. Examples of the basic compound include nitrogen-containing basic compounds, and more specifically, piperidine, aniline and the like. It is particularly preferably piperidine.

The treatment with the basic compound can be carried out by mixing an aqueous solution of the basic compound having an appropriate concentration with the sample DNA which has been reacted with the oxidizing agent and incubating at a temperature of 60 to 100° C. for 1 minute to 1 hour. The concentration of the basic compound may be appropriately selected according to the type of the basic compound, and is preferably 1 to 20% by volume, when pyridine is used.

The occurrence of the cleavage of the sample DNA can be determined by measuring the size of DNA fragment(s) produced after the treatment with the basic compound. The measurement of the size of DNA fragment(s) can be carried out by a well-known method such as the nucleic acid amplification method and the electrophoresis method.

When the nucleic acid amplification method is used, the determination step preferably comprises a step of amplifying the region of the sample DNA which contains the cytosine suspected of being methylated, and a step of detecting the amplified product obtained from the step of amplifying.

The nucleic acid amplification method is the one in which the region containing the cytosine suspected of being methylated in the sample DNA which has been treated with the basic compound is amplified and the size of the amplification product(s) is measured. The nucleic acid amplification method is not specifically limited so long as it is a known method in which a nucleic acid is amplified using primers. For example, PCR method, LAMP method, ICAN method, SDA method and TAS method are mentioned and PCR method is specifically preferable.

The primer may be the one which can complementary bind to the nucleotide sequence region to be amplified in the sample DNA, and allows the amplification of the nucleic acid by the nucleic acid amplification method. The design of the sequence and preparation method for such primers are known by a person skilled in the art.

The detection of the amplification product can be carried out by measuring an efficiency of the nucleic acid amplification (e.g. real-time PCR method), or by subjecting the amplification product to an electrophoresis described below.

The electrophoresis method comprises the electrophoresis of nucleic acid known per se followed by the detection of the nucleic acid. The electrophoresis can be carried out by using a gel of acrylamide, agarose and the like. The detection of nucleic acid can be carried out by using a nucleic acid staining reagent such as ethidium bromide.

(B) Method Comprising Detection of Osmium Complex

When the osmate is used as the oxidizing agent in the above reaction step, the methylated cytosine in the sample DNA and the osmate can form an osmium complex. The methylated cytosine can be detected by detecting this osmium complex. By employing this method, the osmium complex is formed if a cytosine suspected of being methylated in the sample DNA is methylated. Thus, it can be determined that the target cytosine is methylated when the osmium complex is detected. On the other hand, the osmium complex is not formed if a cytosine suspected of being methylated in the sample DNA is a cytosine. With this result, it can be determined that the target cytosine is not methylated.

The method for detecting the presence of the osmium complex includes, for example, a method in which a compound is used which can be a ligand of an osmium ion (hereinafter also referred to as "coordinating compound"). For example, the osmium complex formed from the methylated cytosine and the osmate is reacted with a coordinating compound labeled with a labeling substance, and this label may be detected to detect the methylated cytosine forming the osmium complex. Alternatively, the osmium complex formed from the methylated cytosine and the osmate is reacted with a coordinating compound to form a ligand, the ligand is labeled with a labeling substance, and this label may be detected to detect the methylated cytosine forming the osmium complex.

The coordinating compound is not specifically limited so long as it can be a ligand of the osmium ion. For example, pyridine, bipyridine and phenanthroline are mentioned, among which bipyridine is preferred.

The labeling substance is not specifically limited so long as it can label the ligand. For example, an enzyme label, a fluorescence label, an electrochemical label and a radiolabel are mentioned. Anthraquinone is preferred as the labeling substance because it can be detected easily in electrochemical manner.

A method for preparing the coordinating compound labeled with the labeling substance and a method for labeling the ligand with the labeling substance have been already known. The compounds disclosed in WO 2006/306359 may be used.

The present invention also provides a nucleic acid chip for detecting a methylated cytosine comprising a solid support on which the oligonucleotide is fixed.

In the present embodiment, the nuclei acid chip is not specifically limited so long as it comprises a solid support on which the oligonucleotide is fixed. The solid support may be any solid support which can fix the oligonucleotide. Mention can be made on, for example, polystyrene, gold, glass, magnetic particles such as magnetic iron oxide, microparticles such as zinc sulfide having a quantum dot property.

A method for producing a nucleic acid chip is already known. Namely, the oligonucleotide is contacted with the solid support which is optionally surface treated to have a functional group capable of binding with nucleic acid such as an aldehyde group, an amino group and the like, thereby binding the oligonucleotide on the surface of the solid support.

By using such nucleic acid chip, the sample DNA which has been hybridized with the oligonucleotide on the solid support can be subjected to the above steps of hybridization, oxidizing agent reaction, detection, as well as the solid support can be washed during the processes.

The present invention is further illustrated in detail with the following Examples. However, it should be recognized that the present invention is not limited to these Examples.

EXAMPLE 1

(Preparation of Sample DNAs)
The DNAs represented by the sequences of SEQ ID NOs: 1 and 2 were synthesized and used as the sample DNAs.

```
                                            SEQ ID NO: 1
5'-GAGGCCTTCGCTGGAGTTTCGCCGCCGCAGTCTTCGCCACCAGTGAG
TAC-3'

SEQ ID NO: 2
5'-GAGGCCTTCGCTGGAGTTTMGCMGCMGCAGTCTTCGCCACCAGTGA
GTAC-3'
```

In the sequence of SEQ ID NO: 2, "M" represents methylated cytosine. In this Example, the cytosine which is at position 23 from the 5'-terminal of the sample DNA represented by SEQ ID NOs: 1 and 2 is the target cytosine which is to be detected for methylation.

(Preparation of Oligonucleotides)
The DNAs represented by the sequences of SEQ ID NOs: 3 and 4 were synthesized and used as the oligonucleotides for detecting a methylated cytosine.

```
                                            SEQ ID NO: 3
5'-GTACTCACTGGTGGCGAAGACTGCGGCGGCGAAACTCCAGCGAAGG
CCTC-3'

SEQ ID NO: 4
5'-GTACTCACTGGTGGCGAAGACTGCGGCNGCGAAACTCCAGCGAAGG
CCTC-3'
```

The oligonucleotide represented by SEQ ID NO: 3 has the sequence completely complementary to the sample DNAs represented by SEQ ID NOs: 1 and 2.

The oligonucleotide represented by SEQ ID NO: 4 is the one in which dSpacer for constituting an abasic site is inserted instead of guanine for forming a base pair with cytosine or methylated cytosine at position 23 from 5'-terminal of the sample DNA of SEQ ID NO: 1 or 2. dSpacer is represented as "N" in the nucleotide sequence.

In order to clearly represent the hybridized state of SEQ ID NOs: 1 and 2 and SEQ ID NOs: 3 and 4, SEQ ID NOs: 3 and 4 are specified from 3'-terminal to 5'-terminal and SEQ ID NOs: 1 to 4 are described together in the followings.

```
                                            SEQ ID NO: 1
5'-GAGGCCTTCGCTGGAGTTTCGCCGCCGCAGTCTTCGCCACCAGTGAG
TAC-3'

SEQ ID NO: 2
5'-GAGGCCTTCGCTGGAGTTTMGCMGCMGCAGTCTTCGCCACCAGTGA
GTAC-3'

SEQ ID NO: 3
3'-CTCCGGAAGCGACCTCAAAGCGGCGGCGTCAGAAGCGGTGGTCACT
CATG-5'

SEQ ID NO: 4
3'-CTCCGGAAGCGACCTCAAAGCGNCGGCGTCAGAAGCGGTGGTCACT
CATG-5'
```

As shown in the above, SEQ ID NO: 3 has the nucleotide of guanine at the position complementary to cytosine or methylated cytosine at position 23 from 5'-terminal of SEQ ID NO: 1 or 2, while SEQ ID NO: 4 has the nucleotide of dSpacer.

(Hybridization of Sample DNA with Oligonucleotide)
The sample DNAs of SEQ ID NOs: 1 and 2 were mixed with the oligonucleotides of SEQ ID NO: 3 and 4 with the formulations as shown in Table 1 to prepare Samples 1 to 4. Each sample DNA (SEQ ID NOs: 1 and 2) and oligonucleotide (SEQ ID NOs: 3 and 4) used was the one dissolved in TE buffer (1 mM EDTA, 10 mM Tris-HCl, pH 7.4) to the concentration of 10 μM. The same TE buffer was used as the diluent.

|  | SEQ ID NO: 1 | SEQ ID NO: 2 | SEQ ID NO: 3 | SEQ ID NO: 4 | Diluent | Total amount |
|---|---|---|---|---|---|---|
| Sample 1 | 10 μl |  | 10 μl |  | 80 μl | 100 μl |
| Sample 2 | 10 μl |  |  | 10 μl | 80 μl | 100 μl |
| Sample 3 |  | 10 μl | 10 μl |  | 80 μl | 100 μl |
| Sample 4 |  | 10 μl |  | 10 μl | 80 μl | 100 μl |

Samples 1 to 4 were incubated at 95° C. for 10 minutes, followed by cooling from 95° C. to 35° C. over 30 minutes and further incubation at 35° C. for 30 minutes, so that the sample DNAs were hybridized with the oligonucleotides to form double-stranded DNAs.

(Treatment of Hybridized Products with Oxidizing Agent)
The double-stranded DNAs, which were contained in Samples 1 to 4 obtained from the above hybridization step and were hybridized products of the respective sample DNAs and oligonucleotides, were incubated at room temperature for an hour in the final volume of 50 μl with the final concentrations specified below in "Reaction condition" to carry out the oxidization reaction using potassium osmate as the oxidizing agent.

<Reaction Condition>
5 mM Potassium osmate
100 mM Potassium hexacyanoferrate (III)
1 mM EDTA
100 mM Tris-HCl
10% Methanol
100 nM Double-stranded DNA After the reaction, DNAs were purified from Samples 1 to 4 with DNA purification kit (Qiaquick (product name), QIAGEN) to obtain 100 µl of Samples 1 to 4, respectively.

(Cleavage of Sample DNA with Piperidine)

To 50 µl of Samples 1 to 4 obtained after the osmium oxidization reaction and DNA purification was added piperidine as the basic compound with the final concentration of 10%, and the mixtures were reacted at 90° C. for 20 minutes. The reaction solution was dried in vacuo and solubilized in 25 µl of dH$_2$O. As controls, 50 µl of Samples 1 to 4 were incubated at 90° C. for 20 minutes without adding piperidine, dried in vacuo and solubilized in 25 µl of dH2O.

(Determination of the Occurrence of Cleavage of Sample DNA by Agarose-Gel Electrophoresis)

Samples 1 to 4 obtained from the piperidine treatment and the control samples 1 to 4 were subjected to electrophoresis on an 18% acrylamide gel. After the electrophoresis, the gel was stained with ethidium bromide and analyzed by an imaging analyzer (Molecular Imager FX; BIO-RAD). The results are shown in FIG. 1.

FIG. 1 shows that the sample DNAs hybridized with the oligonucleotide of SEQ ID NO: 3 (Samples 1 and 3) were detected as total-length DNAs irrespective of the treatment with piperidine. This means that the sample DNAs hybridized with the oligonucleotide of SEQ ID NO: 3 were not cleaved by the piperidine treatment. Namely, because the sample DNAs did not contain the methylated cytosine, the sample DNAs were complementary to the oligonucleotide so that the base was not oxidized by the osmium oxidization reaction.

In the sample DNA of SEQ ID NO: 2 which was hybridized with the oligonucleotide of SEQ ID NO: 4 (Sample 4), the amount of the band detected as total-length DNA in the electrophoresis was decreased due to the piperidine treatment. This means that the sample DNA of SEQ ID NO: 2 which was hybridized with the oligonucleotide of SEQ ID NO: 4 was cleaved by the piperidine treatment. This is due to the oxidization of the methslated cytosine by the osmium oxidization reaction because the abasic site is formed at the position of the methylated cytosine which is position 23 from 5'-terminal of the sample DNA of SEQ ID NO: 2. On the other hand, the sample DNA of SEQ ID NO: 1 which was hybridized with the oligonucleotide of SEQ ID NO: 4 and contained in Sample 2 did not show any change in the band detected as the total-length DNA in the electrophoresis even when the piperidine treatment was carried out. This is due to the absence of the cleavage of the sample DNA of SEQ ID NO: 1 hybridized with the oligonucleotide of SEQ ID NO: 4 because the sample DNA does not contain the methylated cytosine at the position of the abasic site.

The sample DNAs contained in Samples 2 and 3, which were not treated with piperidine were not cleaved, and thereby showing no difference in the band detected as the total-length sample DNA in the electrophoresis.

From the above results, it was shown that by using the oligonucleotide which has the abasic site at the position of cytosine suspected of being methylated by insertion of dSpacer, the detection of a methylated cytosine is possible by using the oxidizing agent.

The present application relates to the Japanese Patent Application No. 2007-217263 filed on Aug. 23, 2009, and whose claims, specification, drawing and abstract are incorporated herein by reference.

The invention claimed is:

1. A method for detecting a methylated cytosine comprising the following steps of:
hybridizing a sample DNA with an oligonucleotide which can hybridize with a region of the sample DNA containing a cytosine suspected of being methylated and has an abasic site at the position complementary to the cytosine;
reacting the hybridized sample DNA obtained in the previous step with an oxidizing agent to oxidize the cytosine when it is methylated; and
detecting the oxidized methylated cytosine,
wherein the abasic site is constructed by a nucleotide without a base.

2. The method according to claim 1, wherein the step of detecting comprises the steps of treating the sample DNA having been reacted with the oxidizing agent with a basic compound, and determining the occurrence of a cleavage in the sample DNA which has been treated with the basic compound.

3. The method according to claim 2, wherein the basic compound is piperidine or aniline.

4. The method according to claim 2, wherein the step of determining comprises the steps of amplifying the region of the sample DNA containing the cytosine suspected of being methylated, and detecting the amplified product obtained from the step of amplifying.

5. The method according to claim 1, wherein the oxidizing agent is at least one selected from a permanganate, an osmate, a tungstate, a periodate, hydrogen peroxide solution, t-butyl hydroperoxide, perbenzoic acid, a perbenzoic acid derivative, iodine, a rhenium oxide, peracetic acid, a peracetic acid derivative and a manganese-salen complex.

6. The method according to claim 5, wherein the oxidizing agent is the osmate.

7. The method according to claim 6, wherein the oxidized methylated cytosine forms an osmium complex with the osmate.

8. The method according to claim 1, wherein the oxidizing agent is an osmate; the step of reacting with the oxidizing agent further comprises reacting the sample DNA that has been reacted with the oxidizing agent further with a compound which is ligand of an osmium ion; and the step of detecting detects the methylated cytosine which forms an osmium complex to which the ligand is bound via a coordinate bond.

9. The method according to claim 8, wherein the ligand is labeled with a labeling substance.

10. The method according to claim 8, wherein the ligand is pyridine, bipyridine or phenanthroline.

11. The method according to claim 3, wherein the step of determining comprises the steps of amplifying the region of the sample DNA containing the cytosine suspected of being methylated, and detecting the amplified product obtained from the step of amplifying.

12. The method according to claim 9, wherein the ligand is pyridine, bipyridine or phenanthroline.

* * * * *